(12) United States Patent
Byer et al.

(10) Patent No.: US 11,328,916 B2
(45) Date of Patent: May 10, 2022

(54) USER DEFINED SCALED MASS DEFECT PLOT WITH FILTERING AND LABELING

(71) Applicant: LECO Corporation, St. Joseph, MI (US)

(72) Inventors: Jonathan David Byer, St. Joseph, MI (US); Kevin Matthew Siek, St. Joseph, MI (US)

(73) Assignee: LECO Corporation, St. Joseph, MI (US)

( * ) Notice: Subject to any disclaimer, the term of this patent is extended or adjusted under 35 U.S.C. 154(b) by 888 days.

(21) Appl. No.: 16/081,676

(22) PCT Filed: Mar. 5, 2017

(86) PCT No.: PCT/US2017/020844
§ 371 (c)(1),
(2) Date: Aug. 31, 2018

(87) PCT Pub. No.: WO2017/152160
PCT Pub. Date: Sep. 8, 2017

(65) Prior Publication Data
US 2020/0312641 A1    Oct. 1, 2020

Related U.S. Application Data

(60) Provisional application No. 62/303,813, filed on Mar. 4, 2016.

(51) Int. Cl.
*H01J 49/00*    (2006.01)
*G16C 20/20*    (2019.01)
*G01N 30/72*    (2006.01)

(52) U.S. Cl.
CPC ...... *H01J 49/0036* (2013.01); *G01N 30/7206* (2013.01); *G16C 20/20* (2019.02)

(58) Field of Classification Search
CPC .. H01J 49/0036; G16C 20/20; G01N 30/7206
(Continued)

(56) References Cited

U.S. PATENT DOCUMENTS 7,653,493 B1 *    1/2010   Wang ................. H01J 49/0036
                                                         702/23
8,399,827 B1 *    3/2013   Grothe ............... H01J 49/0036
                                                         250/282

(Continued)

OTHER PUBLICATIONS

International Search Report dated Jul. 21, 2017, relating to International Application No. PCT/US2017/020844.

*Primary Examiner* — Michael Maskell
(74) *Attorney, Agent, or Firm* — Honigman LLP

(57) ABSTRACT

A method of determining mass defect plots with user-defined mass scaling, filtering, and labeling in a mass spectrometer is described. An implementation of the method comprises, (i) generating a mass defect plot from the data, (ii) filtering all ions in the mass defect plot that do not have an associated isotopologue ion, (iii) selecting an unidentified ion, (iv) determining an isotope pattern of the unidentified ion, (v) identifying one or more elements indicated by the isotope pattern for the unidentified ion; (vi) searching formulas containing one or more elements indicated by the isotope pattern for the unidentified ion, (vii) determining a chemical formula of the identified ion, and (viii) displaying the chemical formulas for the unidentified ion on a screen.

57 Claims, 11 Drawing Sheets

(58) Field of Classification Search
USPC .................. 250/281, 282; 702/22–28, 30
See application file for complete search history.

(56) References Cited

U.S. PATENT DOCUMENTS

| | | | | |
|---|---|---|---|---|
| 2007/0114373 A1* | 5/2007 | Zweigenbaum | .... | H01J 49/0036 250/282 |
| 2007/0284520 A1* | 12/2007 | Yamamoto | .......... | H01J 49/0036 250/282 |
| 2008/0001079 A1* | 1/2008 | Wang | .................. | H01J 49/0036 250/282 |

* cited by examiner

USER DEFINED SCALED MASS DEFECT PLOT WITH FILTERING AND LABELING

TECHNICAL FIELD

This disclosure relates to generating mass defect plots with user-defined mass scaling, filtering, and labeling.

BACKGROUND

Mass spectrometry (MS) is an analytical technique that can be used for determining the mass of an ion, which may be used to interpret information about a compound such as elucidating the chemical structures of molecules, including small metabolites and other chemical compounds. Mass spectrometry generally includes ionizing chemical compounds to generate charged molecules or molecule fragments and then measuring their mass-to-charge ratios. In a typical MS procedure, a sample loaded onto a mass spectrometer undergoes vaporization and the components of the sample are ionized to form charged particles (ions). The ions are typically accelerated by an electric field for computation of the mass-to-charge ratio (m/z) of the particles based on the details of motion of the ions as they move through electromagnetic fields. The ions may be sorted by a mass analyzer according to their mass-to-charge ratio (m/z) and detected measuring the value of an indicator quantity and providing data for calculating the abundances of each ion present. The calculated mass of each ion may change or drift during operation of the mass spectrometer, due to various factors.

Every isotope has a defined mass defect depending on its relative nuclear binding energy to carbon-12. Each nuclide has a different mass defect and every molecule of a specific elemental composition will have the mass uniquely characteristic of that elemental composition. The mass defect is determined by the difference between the exact mass of the isotope in question and the normal integer mass of the isotope in question. The specific mass defect may be used to assist in identifying the exact chemical formula. This application presents a method for filtering and labeling of specific isotopes and chemical compounds by mass defect based on accurate mass determination.

SUMMARY

One aspect of the disclosure provides a method of constructing a filtered mass defect plot based on accurate mass data acquired from a mass spectrometer. In an implementation, the filtered mass defect plot may be a halogen filtered mass defect plot. The method includes generating a mass defect plot from data obtained from the mass spectrometer, filtering all ions in the mass defect plot that do not have an associated confirmatory isotopologue (e.g. an M+2 or M−2 ion), selecting an unidentified ion, and determining an isotope pattern of the unidentified ion. The method further includes identifying one or more elements indicated by the unidentified ion, searching formulas containing one or more elements indicated by the isotope pattern for the unidentified ion, determining a chemical formula of the unidentified ion, and displaying the chemical formula for the unidentified ion on a screen.

Implementations of the disclosure may include one or more of the following optional features. In some implementations, the method includes receiving a user selection of an ion, displaying the selected ion as an extracted ion chromatogram±mass tolerance, and identifying one or more chromatographic peak(s) corresponding to the extracted ion chromatogram±mass tolerance. The method may also include identifying homologous series and RDBE related species related to the unidentified ion. The homologous series may further include chlorine and or bromine. The RDBE related species may include deuterium and/or hydrogen.

In some examples, the data is raw data from the mass spectrometer. The data may be deconvoluted data from the mass spectrometer. The method may also include labeling the chemical formulas for the unidentified ion on the screen. The method may further include assigning a color to the unidentified ion on the screen.

In some implementations, the mass defect plot is a chlorine substituted for hydrogen (Cl—H) mass defect plot. The mass defect plot may also be a bromine substituted for hydrogen (Br—H) mass defect plot. Filtering all ions in the mass defect plot that do not have an associated confirmatory isotopologue (e.g. an M+2 or M−2) ion may further include filtering the mass defect with a specific tolerance and relative abundance. Filtering all ions in the mass defect plot that do not have an associated M+2 or M−2 ion may also include filtering all ions that do not match $Br_x$ isotope pattern, where x is an integer between 1 and 15 inclusive. Filtering all ions in the mass defect plot that do not have an associated M+2 or M−2 ion may also include filtering all ions that do not match $Cl_y$ isotope pattern, where y is an integer between 1 and 15 inclusive. In some examples, filtering all ions in the mass defect plot that do not have an associated M+2 or M−2 ion includes filtering all ions that do not match $Br_xCl_y$ isotope pattern. Filtering all ions in the mass defect plot that do not have an associated confirmatory isotopologue may further include filtering by determining a spacing tolerance.

The spacing tolerance may be based on a static m/z distance between the first signal and the second signal. The spacing tolerance may be based on a statistical m/z confidence interval determined from the number of ions in the first signal and the number of ions in the second signal. The spacing tolerance may be based on a statistical m/z confidence interval may be approximately 2.8. The spacing tolerance may be limited by user input.

In some examples, filtering all ions in the mass defect plot that do not have an associated confirmatory isotopologue includes filtering by relative abundance. The relative abundance may be determined for M+1 signals. Determining the relative abundance for M+1 signals may further include determining a maximum predicted count of an M+1 element based on an intensity of a putative M+1 signal, an intensity of a putative monoisotopic signal, and a terrestrial natural abundance of the M+1 element. The M+1 element may be carbon, nitrogen, silicon, or any other element with a naturally occurring M+1 isotope.

Determining the relative abundance for M+2 signals may include determining a maximum predicted count of an M+2 element based on an intensity of a putative monoisotopic signal, an intensity of a putative M+2 signal, and a terrestrial natural abundance of the M+2 element. In some examples, determining the relative abundance for M+2 signals further includes determining a maximum predicted count of an M+2 element based on an intensity of a putative monoisotopic signal, an intensity of a putative M+2 signal, an intensity of a putative M+4 signal and a terrestrial natural abundance of the M+2 element. Determining the relative abundance for M+2 signals may also include determining a maximum predicted count of an M+2 element based on an intensity of a putative monoisotopic signal, an intensity of a putative M+4 signal, an intensity of a putative M+6 signal and a terrestrial natural abundance of the M+2 element. Determining the relative abundance for M+2 signals may further include determining a maximum predicted count of an M+2 element based on an intensity of a putative monoisotopic signal, an intensity of a putative M+6 signal, an intensity of a putative M+8 signal and a terrestrial natural abundance of the M+2 element. In some implementations, determining the relative abundance for M+2 signals includes determining if one or more analytes contain both chlorine and bromine, and if the one or more analytes contain both chlorine and bromine, determining a maximum predicted count of an M+2 element based on the terrestrial natural abundance of $^{37}Cl$, and the terrestrial natural abundance of $^{81}Br$.

Another aspect of the disclosure provides a method of constructing a filtered mass defect plot based on accurate mass data acquired from a mass spectrometer. The device includes a display, data processing hardware in communication with the display, and memory hardware in communication with the data processing hardware. The memory hardware stores instructions, that when executed on the data processing hardware cause the data processing hardware to perform operations. The operations include generating a mass defect plot from data obtained from a mass spectrometer, filtering all ions in the mass defect plot that do not have an associated confirmatory isotopologue, selecting an unidentified ion, and determining an isotope pattern for an isotopic cluster of the unidentified ion. The operations also include identifying one or more elements contained within the isotope pattern for the unidentified ion, searching formulas containing one or more elements identified by the isotope pattern for the unidentified ion, determining a chemical formula of the isotopic cluster related to the unidentified ion, and displaying the chemical formulas for the unidentified ion on a display.

This aspect may include one or more of the following optional features. The operations may include receiving a user selection of an ion, displaying the selected ion as an extracted ion chromatogram±mass tolerance, and identifying one or more chromatographic peak(s) corresponding to the extracted ion chromatogram±mass tolerance. The operations may further include identifying homologous series and RDBE related species related to the unidentified ion. The homologous series may include chlorine and/or bromine. The RDBE related species may include deuterium and/or hydrogen.

In some examples, the data is raw data from a mass spectrometer. The data may be deconvoluted data from a mass spectrometer. The operations may include labeling the chemical formulas for the unidentified ion on the display. The operations may also include assigning a color to the unidentified ion on the display.

In some implementations, the mass defect plot is a chlorine substituted for hydrogen (Cl—H) mass defect plot. The mass defect plot may also be a bromine substituted for hydrogen (Br—H) mass defect plot. Filtering all ions in the mass defect plot that do not have an associated confirmatory isotopologue (e.g. an M+2 or M−2) ion may further include filtering the mass defect with a specific tolerance and relative abundance. Filtering all ions in the mass defect plot that do not have an associated M+2 or M−2 ion may also include filtering all ions that do not match $Br_x$ isotope pattern, where x is an integer between 1 and 15 inclusive. Filtering all ions in the mass defect plot that do not have an associated M+2 or M−2 ion may also include filtering all ions that do not match $Cl_y$ isotope pattern, where y is an integer between 1 and 15 inclusive. In some examples, filtering all ions in the mass defect plot that do not have an associated M+2 or M−2 ion includes filtering all ions that do not match $Br_xCl_y$ isotope pattern. Filtering all ions in the mass defect plot that do not have an associated confirmatory isotopologue may further include filtering by determining a spacing tolerance.

The spacing tolerance may be based on a static m/z distance between the first signal and the second signal. The spacing tolerance may be based on a statistical m/z confidence interval determined from the number of ions in the first signal and the number of ions in the second signal. The spacing tolerance may be based on a statistical m/z confidence interval may be approximately 2.8. The spacing tolerance may be limited by user input.

In some examples, filtering all ions in the mass defect plot that do not have an associated confirmatory isotopologue includes filtering by relative abundance. The relative abundance may be determined for M+1 signals. Determining the relative abundance for M+1 signals may further include determining a maximum predicted count of an M+1 element based on an intensity of a putative M+1 signal, an intensity of a putative monoisotopic signal, and a terrestrial natural abundance of the M+1 element. The M+1 element may be carbon, nitrogen, silicon, or any other element with a naturally occurring M+1 isotope.

The relative abundance may also be determined for M+2 signals. The operation determining the relative abundance for M+2 signals may include, determining a maximum predicted count of an M+2 element based on an intensity of a putative monoisotopic signal, an intensity of a putative M+2 signal and a terrestrial natural abundance of the M+2 element. The operation determining the relative abundance for M+2 signals may also include determining a maximum predicted count of an M+2 element based on an intensity of a putative monoisotopic signal, an intensity of a putative M+2 signal, an intensity of a putative M+4 signal and a terrestrial natural abundance of the M+2 element. The operation determining the relative abundance for M+2 signals may further include, determining a maximum predicted count of an M+2 element based on an intensity of a putative monoisotopic signal, an intensity of a putative M+4 signal, an intensity of a putative M+6 signal and a terrestrial natural abundance of the M+2 element. In some examples, the operation determining the relative abundance for M+2 signals includes, determining a maximum predicted count of an M+2 element based on an intensity of a putative monoisotopic signal, an intensity of a putative M+6 signal, an intensity of a putative M+8 signal and a terrestrial natural abundance of the M+2 element. The operation determining the relative abundance for M+2 signals may further include determining if one or more analytes contain both chlorine and bromine, and if the analytes contain both chlorine and bromine, determining a maximum predicted count of an M+2 element based on the terrestrial natural abundance of $^{37}Cl$, and the terrestrial natural abundance of $^{81}Br$.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

Figure 1:
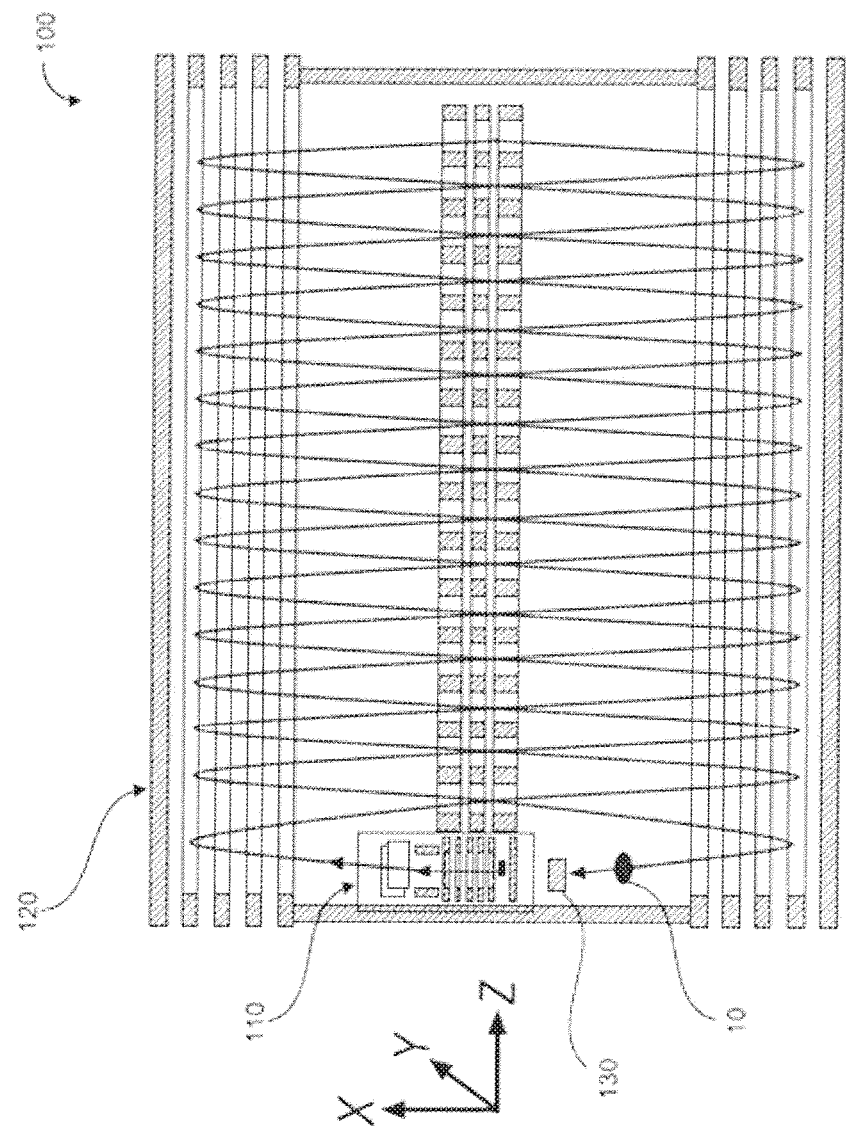
FIG. 1 is a schematic view an exemplary time-of-flight mass spectrometer (TOF-MS) mass analyzer.

Referring to FIG. 1, in a time-of-flight (TOF) mass spectrometer (MS) 100, a mass M of an ion 10 can be determined by accelerating ion(s) 10 along a flight path (e.g., using an electric field), measuring a flight time T of the ion(s) 10, and determining the mass M of the ion(s) 10 by using a relationship of the time-of-flight T as a function of the mass M (e.g., a mass calibration equation). For example, the time-of-flight T of each ion 10 can be determined using the following equation:

$$T = \frac{d}{\sqrt{2U}} \sqrt{\frac{M}{z}}, \quad (1)$$

where d is a flight path length of the ion 10, M is a mass of the ion 10, z is a charge of the ion 10, and U is an electric potential difference (voltage) used to accelerate the ion 10. Accelerating ions 10 with a known electric field strength U, results in each ion 10 having the same kinetic energy as any other ion 10 that has the same charge z. Since a velocity of the ion 10 depends on its mass-to-charge ratio (m/z), the time that it subsequently takes for an ion 10 to travel along the flight path and reach a detector 130 (i.e., time-of-flight T) can be measured. Heavier ions 10 travel relatively slower and relatively longer flight times T than lighter ions 10. The measurements determined by the detector 130 are returned as data 140 (see FIG. 2) to the computer system 1100 for processing (see FIG. 2).

FIG. 1 provides a schematic view of an exemplary time-of-flight mass spectrometer (TOF-MS) system 100 that includes an ion source assembly 110 (e.g., an accumulating ion source with transfer ion optics and an orthogonal accelerator) in communication with a TOF analyzer 120 (e.g., a planar multi-reflecting TOF (M-TOF) analyzer) and a detector 130. The ion source assembly 110 accelerates ions 10 (e.g., packets of ions) through the TOF analyzer 120 having a flight path and corresponding flight path length d and into the detector 130.

Figure 2:
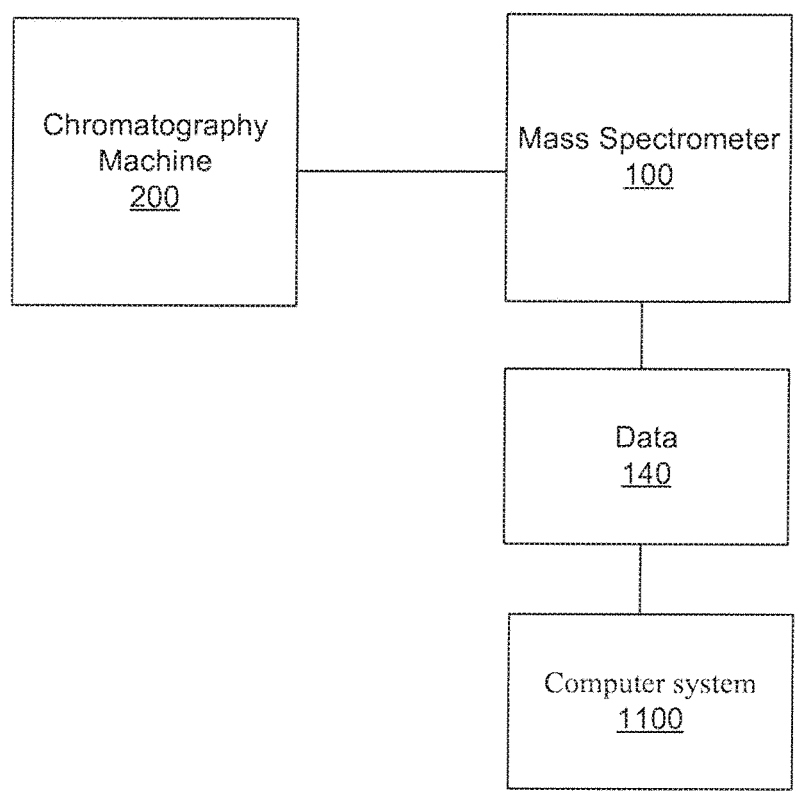
FIG. 2 is a schematic view a TOF-MS and sample introduction gas chromatograph system.

FIG. 2 provides a schematic view of a TOF-MS 100 and gas chromatograph system 200. The gas chromatograph 200 utilizes a capillary column, multiple capillary columns or column set with given dimensions and phase properties. In some examples, the gas chromatograph 200 may be a liquid chromatograph. A sample is introduced into the column, and depending on the difference in the chemical properties of the molecules in the mixture and the affinity of the molecules to remain stationary within the column, the column promotes separation of the molecules. The sample may be introduced by direct insertion probes or pyrolysis. In some examples, the sample is introduced without a chromatography. The molecules elute from the column at different times based on the retention time. The TOF-MS 100 captures, ionizes, accelerates, deflects, focuses and detects the ionized molecules separately as they are released from the gas chromatograph 200. The TOF-MS 100 and gas chromatograph system 200 are given for an example and context, it should be understood that any system or mass spectrometer capable of determining the accurate mass of ions may be suitable, including systems that permit non-chromatographic or direct sample introduction.

Figure 3:
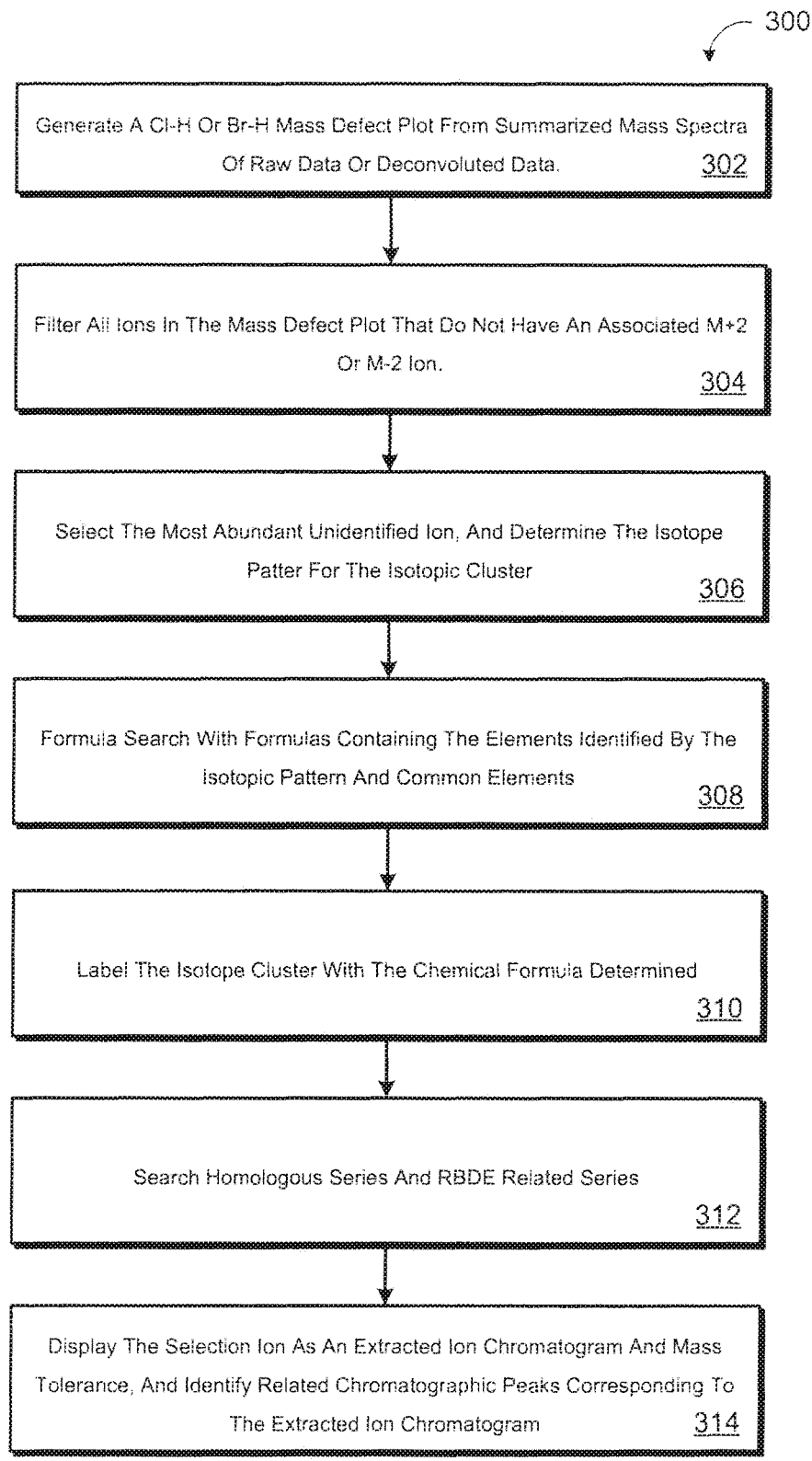
FIG. 3 provides an exemplary arrangement of operations for labeling a mass defect plot (MDP) with halogen filtering.

FIG. 3 provides an exemplary arrangement of operations 300 for labeling a mass defect plot (MDP) 900 with halogen filtering. While halogen filtering is exemplary described herein, it is to be appreciated that it is but one embodiment and other elements or combinations of elements may be utilized. At block 302, the operations 300 include generating a Cl—H or Br—H mass defect plot from the summed mass spectra of raw data or deconvoluted data (sum of individual peak mass spectrum). The data 140 may be determined from data 140 provided by the TOM-MS 100 and plotted on a scale of the atomic mass defect (IUPAC) or other suitable scale. At block 304, the operations 300 include filtering all ions 10 in the MDP 900 that do not have an associated M+2 or M−2 ion (Mass difference of 1.997050 Da for chlorine, or 1.997953 Da for bromine) with a scaled mass defect within a specified tolerance. An example tolerance may be 0.0007 Da, and relative abundance±15% that does not match a theoretical $Br_x$, $Cl_y$, or $Br_xCl_y$, (where x may be an integer from 1 to 15 inclusive and y may be an integer from 1 to 15 inclusive) isotope pattern 150 in at least one embodiment of the invention. Alternatively, tolerances may be calculated as described below in the relation to FIGS. 4 and 5.

At block 306, the operations 300 include selecting the most abundant unidentified ion 10, and determining the isotope pattern 150 for the isotopic cluster 152 i.e., $Br_2$ or $BrCl_2$, etc. At block 308, the operations 300 include formula searching for the formula containing the elements identified by the isotope pattern 150, in addition to other common elements using, for example, standard combinatorial approaches. Other common elements include, but are not limited to Carbon, Hydrogen, Nitrogen, Oxygen, Sulfur, and/or Phosphorus, etc. At block 308, the operations 300 include labeling the isotope cluster 152 with the chemical formula determined. In some embodiments, the operations 300 include assigning a unique color, symbol or identifier to the isotope cluster 152. At block 310, the operations include labeling the isotope cluster 152 with the chemical formula determined in block 308. At block 312, the operations include searching homologous series (±Cl or ±Br), and RDBE related species (±H or ±2H) and labeling with the same color as the isotope cluster 152 identified and colored in block 310. In some embodiments, at block 314, the operations include showing the selected ion 10 as an extracted ion chromatogram±mass tolerance (i.e., 207.1547±5 ppm or ±0.001 Da), and identifying the chromatographic peak(s) corresponding to the extracted ion chromatogram. In some embodiments, the operation blocks 306 through 314 are repeated until all ions in the MDP 900 are identified.

Figure 4:
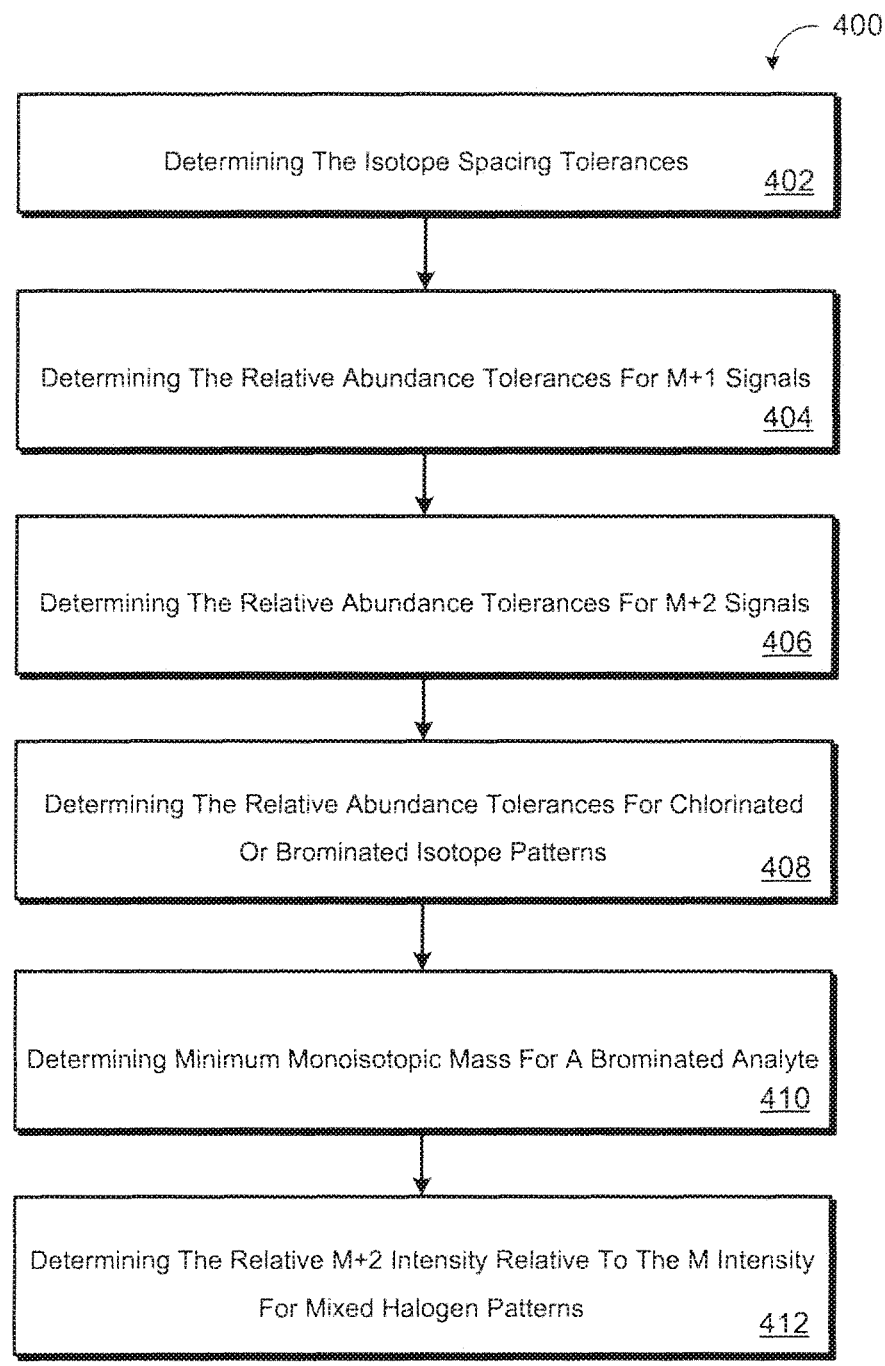
FIG. 4 provides an example method 400 to determine spacing signals and relative isotopic abundance.

FIG. 4 provides an example method 400 to determine spacing signals and relative isotopic abundance. At block 402 the spacing tolerance Tm is determined. A confidence interval, or m/z tolerance ($T_m$), for the difference between centroids of two recorded spectral signals of similar m/z is given by Equation 2:

$$T_m = (\pm K_m)(0.42466)(m)(R_{FWHM})^{-1}[(n_1)^{-1} + (n_2)^{-1}]^{1/2} \quad (2)$$

where $K_m$ is the m/z confidence interval width divided by σ, 0.42466 is σ divided by Full Width at Half-Maximum height (FWHM), m is the m/z centroid of spectral signal 1 approximately equal to the m/z centroid of spectral signal 2, $R_{FWHM}$ is the expected resolving power at half-maximum height of the signals, $n_1$ is the number of ions 10 in the spectral signal 1 (the more intense signal) and $n_2$ is the number of ions 10 in spectral signal 2 (the less intense signal).

To simplify implementation and enhance automated deisotoping speed, parameters may be eliminated via simplifying approximations. Eliminating $n_1$ or $n_2$ permits a single $T_m$ to be used for each stick, rather than a different $T_m$ for each pair of sticks compared. By definition, $n_1$ will not be less than $n_2$, thus $n_1$ will not contribute more to $T_m$ than $n_2$, and eliminating $n_1$ is more prudent than eliminating $n_2$. Assuming $n_1$ is approximately equal to $n_2$ and substituting $n_2$ for $n_1$ in Equation 2 yields Equation 3:

$$T_m = (\pm K_m)(0.42466)(m)(R_{FWHM})^{-1}(2)^{1/2}(n_2)^{1/2} \quad (3)$$

The number of ions, ($n_2$), is related to the spectral area of signal 2 as in Equation 4:

$$n_2 = (a_2)(i_2) \quad (4)$$

where, $a_2$ is the spectral area of signal 2, and $i_2$ is the ions 10 per area expected at the mass of signal 2.

When tuning the detector, ions 10 per area is estimated for the tune mass. It is expected that some detectors may register weaker signals for heavier, hence slower ions 10 and stronger signals for lighter, hence faster ions 10. For such detectors, if detector response is directly proportional to ion 10 velocity and ions per area is estimated for a single tune mass, then the ions 10 per area expected at the mass of signal 2, ($i_2$), is related to the ions 10 per area at the tune mass by Equation 5:

$$i_2 = (i_{tune})(m/m_{tune})^{1/2} \quad (5)$$

where, $i_{tune}$ is the ions 10 per area for the tune mass by detector tune or measurement, and $m_{tune}$ is the m/z of the tune mass used by detector tune or detector measurement.

Substituting Equation 5 into Equation 4, substituting the result into Equation 3, and partially simplifying yields Equation 6:

$$T_m = (\pm K_m)(2)^{1/2}(0.42466)(m)(R_{FWHM})^{-1}[(a_2)(i_{tune})(m/m_{tune})^{1/2}]^{-1/2} \quad (6)$$

Further simplification would show that the m/z tolerance, ($T_m$), is expected to vary with the ¾ power of the observed m/z (m). Thus, for masses heavier than the tune mass, the $T_m$ predicted by Equation 6 will be narrower than the $T_m$ predicted by assuming detector response is independent of ion mass. Likewise, for masses lighter than the tune mass, the $T_m$ predicted by Equation 6 will be wider than the $T_m$ predicted by assuming detector response is independent of ion mass. Note that not all detectors register weaker signals for heavier, hence slower ions 10 and stronger signals for lighter, hence faster ions 10, thus for some detectors, the m/z tolerance will vary linearly with observed m/z, or the m/z tolerance will as a different function of m/z.

A practical value for $K_m$ is about 2.8, corresponding to about 99.5% confidence. Multiplying 2.8 by the square root of 2 gives a convenient value of about 4. The recommended spacing tolerance for detectors where response is directly proportional to ion velocity is then given by Equation 7:

$$T_m = (\pm 4)(0.42466)(m)(R_{FWHM})^{-1}[(a_2)(i_{tune})(m/m_{tune})^{1/2}]^{-1/2} \quad (7)$$

To permit facile substitution of resolution at other peak heights into Equation 7, the constant converting $R_{FWHM}$ to σ (0.42466) is not combined with the confidence interval factor (±4).

Figure 5:
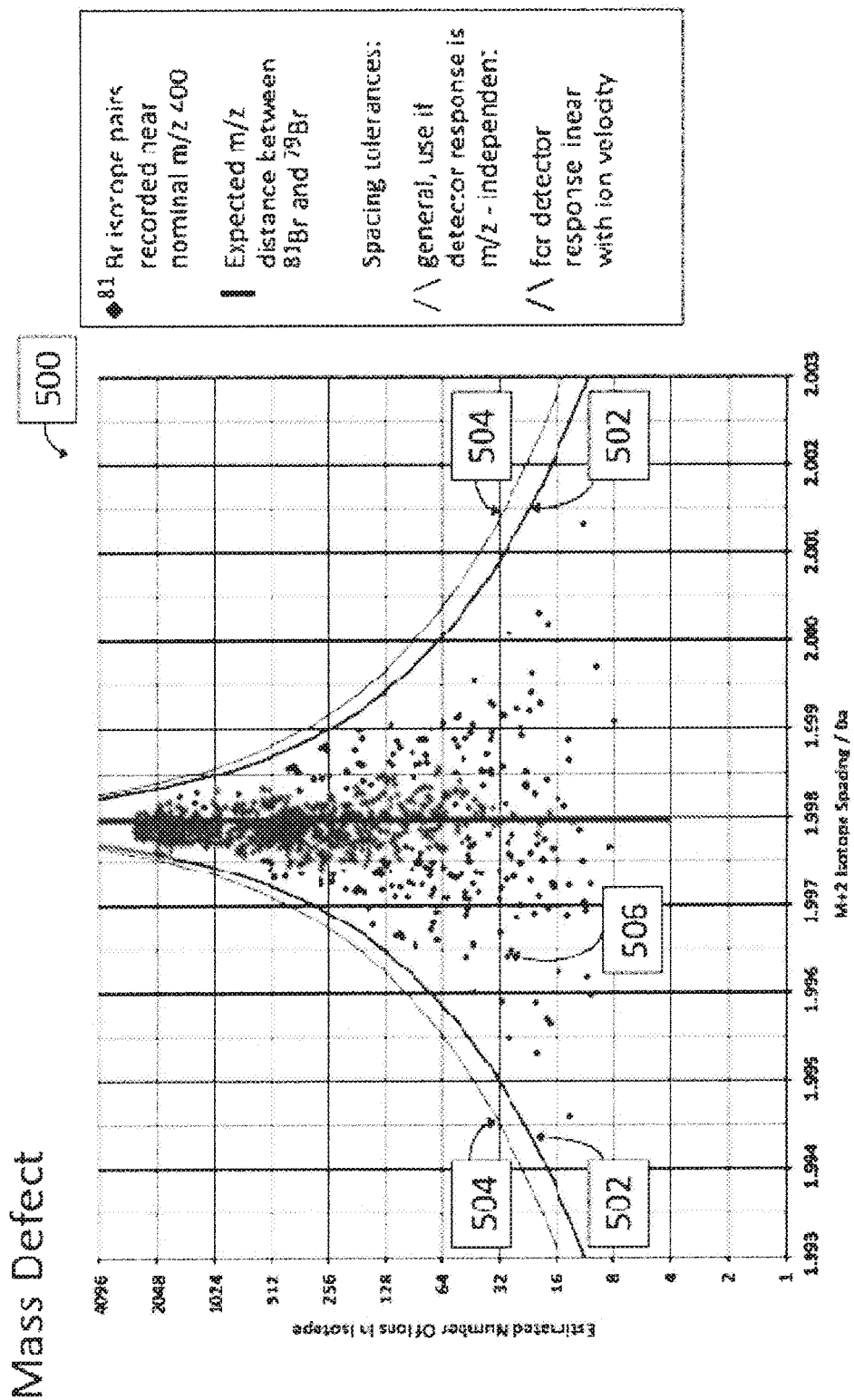
FIG. 5 shows m/z spacing distribution of Br isotopologues amongst multiple spectra of the molecular ion of $C_4Br_4S$ (nominal m/z 400)

Empirical verification of spacing tolerances predicted by Equation 7 is illustrated in FIG. 5. Replicate injections of tetrabromobenzothiophene were recorded, spacing of all bromine isotopologues of the molecular ion in all spectra of all injections was calculated, and estimated number of ions 10 in the minor isotopologue was plotted against spacing. Spacing tolerances predicted by Equation 7 are shown by the curve 502. For comparison, spacing tolerances predicted using the linear-with-m model (i.e. the model assuming detector response is independent of m/z), are shown by the curve 504. A total of 1230 individual bromine isotopologue pairs 506 are shown in the plot. FIG. 5 shows spacing of Br isotopologues for the molecular ion of $C_4Br_4S$ (nominal m/z 400). The ions 10 per area were measured at nominal m/z 219. Expected $R_{FWHM}$ at m/z 400 is 35,000.

Additional adjustments to spacing tolerances may be implemented to avoid statistically-based tolerances that are too narrow at very large n or small m/z, and to avoid tolerances that are too wide at very low n and large m/z. To avoid the latter case, tolerance width may be limited to the width corresponding to a number of ions 10 that can be quantitated with reasonable accuracy. Expected CV for the area of 25 ions 10 is about 20%; the corresponding upper limit for tolerance width is captured in Equation 8:

$$T_m = (\pm 4)(0.42466)(m)(R_{FWHM})^{-1}\{MAX[(25),(a_2)(i_{tune})(m/m_{tune})^{1/2}]\}^{-1/2} \quad (8)$$

Capping the tolerance width at the width expected for 25 ions 10 would reject 2 of 1230 isotope pairs plotted in FIG. 5. In both pairs that would be rejected, the minor isotope has a total of less than 16 ions.

At very large nor small m/z, non-statistical contributions to isotope signal spacing may dominate statistical contributions. A final adjustment may be to override the $T_m$ predicted by Equation 8 with a user-specified minimum tolerance, as in Equation 9:

$$T = MAX[T_{user}, T_m] \quad (9)$$

A reasonable default for $T_{user}$=1.5 mDa.

At block 404, the method 400 includes determining the relative abundance tolerances for M+1 signals. After putative pairs of isotopologues are found within the preceding spacing tolerances, reasonable relative abundance tolerances may be established by considering the element counts predicted by the pairs of putative isotopologues.

For GC-amenable analytes typically encountered in petroleum, biological, food, or environmental samples, the principal contributions to total M+1 relative abundance are $^{13}C$, $^{15}N$, $^{29}Si$, and $^{33}S$, with minor contributions from $^{17}O$ and $^{2}H$. As boron-containing and metal-containing analytes are rarely encountered in the preceding sample types, such analytes are not considered in the following discussion.

Of likely M+1 contributors, $^{29}Si$ is expected to contribute the greatest relative abundance per unit of mass. Thus, for any putative isotope duster in a spectrum, the most tolerant assumed possible elemental composition is pure terrestrial silicon. Silicon count is then predicted from relative abundance of the putative M+1 signal. For a true M+1 signal, the predicted silicon count including an appropriate tolerance cannot exceed the measured monoisotopic mass divided by 28.

Prediction of silicon count from M+1 relative abundance is given in Equation 10, and generalized to any "M+1" element in Equation 11:

$$Si = [M+1][M]^{-1}[0.0508]^{-1} \quad (10)$$

where Si is the predicted maximum silicon count in the formula, [M+1] is the intensity of putative M+1 signal, [M] is the intensity of putative monoisotopic signal, and 0.0508 is the terrestrial natural abundance of $^{29}$Si.

$$C_{M+1} = [M+1][M]^{-1}[A]^{-1} \quad (11)$$

where, $C_{M+1}$ is the predicted max. count of an "M+1" element (principally C, N, Si), [M+1] is the intensity of putative M+1 signal, [M] is the intensity of putative monoisotopic signal, and A is the terrestrial natural abundance of an element.

Ion statistics fundamentally limit the certainty of predicted element counts given by Equation 11. A confidence interval, or element count tolerance ($T_c$), about the predicted element count (C) is given by Equation 12:

$$T_c = (\pm K_c)(C)(n_p)^{-1/2}[2+(AC)+(AC)^{-1}]^{1/2} \quad (12)$$

where, C is the predicted count of an element, $K_c$ is the element count confidence interval/σ; a reasonable value is 2.8, corresponding to about 99.5% confidence, and $n_p$ is the total number of ions 10 in the pair of putative isotopologue signals; note that equivalent renditions of Equation 12, using $n_M$ or $n_{M+1}$ in place of $n_p$ could be derived by using the relationships $n_M + n_{M+1} = n_p$ and $n_{M+1}/n_M = AC$.

Thus, a provisionally assigned M+1 signal found by m/z spacing may be rejected as false M+1 assignment if the predicted maximum silicon count (from Equation 10) minus the element count tolerance ($T_c$, from Equation 12) is greater than the measured monoisotopic mass divided by 28. If silicon-containing compounds are not analytes of interest in a particular analysis, the M+1 relative abundance threshold may be based on pure terrestrial carbon. In this case, predicted carbon count would be given by Equation 11, where A=0.0108. This predicted carbon count minus the carbon count tolerance from Equation 12 should not exceed the measured monoisotopic mass divided by 12.

At block 406, the method 400 includes determining relative abundance tolerances for M+2 signals. Testing putative $^{34}$S signals should be similar to testing putative M+1 signals; the predicted sulfur count minus the sulfur count tolerance from Equation 12 should not exceed the measured monoisotopic mass divided by 32.

Chlorinated and brominated analytes exhibit strong characteristic isotope patterns with multiple detectable isotopologues in a series (M, M+2, M+4, M+6, . . . ). Within a valid series of $^{37}$Cl, $^{81}$Br, or mixed halogen isotopologues, there will always be at least one adjacent halogen isotopologue pair of relative abundance difference not less than the terrestrial natural abundance of $^{37}$Cl, subject to statistically valid relative abundance tolerances. Thus, a series of putative halogen isotopologues should be rejected if all pairs of adjacent members yield a predicted chlorine count less than one minus the tolerance given by Equation 12. Alternatively, more thorough approaches to testing putative halogen patterns are possible, but may be computationally cumbersome. Some of the details are discussed below.

At block 408, the method 400 includes determining the alternative relative abundance tolerances for chlorinated or brominated isotope patterns. Chlorinated and brominated analytes can exhibit strong isotope clusters with multiple even (M, M+2, M+4, etc.) isotopologues of significant abundance (>10% relative to the most abundant isotopologue). Putative members of such strong isotope clusters may be confirmed or rejected by requiring predicted element counts to agree for adjacent pairs of putative isotopologues. For a typical organic compound that contains chlorine or bromine but not both elements, Equation 11 may be extended to higher isotopologue pairs as in Equations 13 to 16, and can be further generalized if desired.

$$C_{M+2} = [M+2][M]^{-1}[A]^{-1} \quad (13)$$

$$C_{M+2} = 1 + (2)[M+4][M+2]^{-1}[A]^{-1} \quad (14)$$

$$C_{M+2} = 2 + (3)[M+6][M+4]^{-1}[A]^{-1} \quad (15)$$

$$C_{M+2} = 3 + (4)[M+8][M+6]^{-1}[A]^{-1} \quad (16)$$

where, $C_{M+2}$ is the predicted maximum count of an "M+2" element (principally Cl, Br), [M] is the intensity of putative monoisotopic signal, [M+2] is the intensity of putative M+2 signal, [M+4] is the intensity of putative M+4 signal, [M+6] is the intensity of putative M+6 signal, [M+8] is the intensity of putative M+6 signal, and A is the terrestrial natural isotopic abundance (principally $^{37}$Cl, $^{81}$Br).

The tolerance from Equation 12 can be validly applied to Equation 13 for a putative M+2/M pair, but may underestimate the uncertainty in relative abundance for higher isotopologue pairs. Valid generalization of Equation 12 to higher isotopologue pairs may be computationally cumbersome. A more practical approach is to predict chlorine or bromine count ($C_{M+2}$) for each pair of adjacent putative M+2 isotopologues and accept a putative isotope cluster if predicted chlorine or bromine count is consistent for all adjacent isotopologue pairs. Loose tolerances should be applied; requiring predicted element counts to agree to within a factor of 2 is reasonable. The above may be used to determine the MDP 900 that do not have an associated M+2 or M−2 ion.

At block 410, the method includes determining minimum monoisotopic mass for a brominated analyte using virtual monoisotopic bromine. Highly brominated analytes can exhibit monoisotopic signals markedly weaker than the most abundant isotopologue. For highly brominated analytes, the likelihood of a quantifiable most abundant isotopologue belonging to an undetectable monoisotopic signal warrants permitting virtual bromine isotopologues to be considered. A reasonable maximum number of virtual bromine isotopologues to add is twice the sum of the number of detected bromine isotopologues minus two. Thus, if three bromine isotopologues are detectable, the detected isotopologue of lowest mass may be tested as M (no virtual bromine isotopologues) or M+2 (two virtual bromine isotopologues; one on each side of the detected isotope cluster). If four bromine isotopologues are detectable, the detected isotopologue of lowest mass may be tested as M (no virtual bromine isotopologues), M+2 (two virtual bromine isotopologues; one on each side of the detected isotope cluster), or M+4 (four virtual bromine isotopologues; two on each side of the detected isotope cluster).

The monoisotopic mass must be sufficient to support the number of bromines predicted by the isotope cluster, plus the number of carbons required to support additional bromines beyond two. Minimum monoisotopic mass for a brominated analyte is given by Equation 17, Equation 18, and Equation 19.

$$\text{Mass}_{min}=(79)(C_{Br})+(12)(C_{Cmin}) \quad (17)$$

where, $\text{Mass}_{min}$ is the minimum monoisotopic mass for a brominated analyte, $C_{Br}$ is the Br count predicted by the number of Br isotopologues (Eq. 18), and $C_{Cmin}$ is the Minimum C count required to support the Br count (Eq. 19).

$$C_{Br}=(\text{sum of detected and virtual bromine isotopologues})-1 \quad (18)$$

$$C_{Cmin}=(C_{Br}-2)(2)^{-1} \quad (19)$$

Any fractional value of $C_{Cmin}$ in Equation 19 is always rounded up to the greater integer. Virtual bromine isotopologues cannot be added if the resulting monoisotopic mass would be less than $\text{Mass}_{min}$ from Equation 17.

At block 412, the method 400 includes determining the relative M+2 intensity relative to the M intensity for mixed halogen patterns. Analytes containing both Cl and Br will exhibit isotope patterns that do not yield consistent predicted element counts using the form of Equations 12 to 16. For such mixed halogens, total M+2 intensity relative to M intensity is given by Equation 20:

$$[M+2][M]^{-1}=A_{Cl}C_{Cl}+A_{Br}C_{Br} \quad (20)$$

where, $A_{Cl}$ is the terrestrial natural abundance of $^{37}Cl$, $C_{Cl}$ is the chlorine count in the formula, $A_{Br}$ is the terrestrial natural abundance of $^{81}Br$, and $C_{Br}$ is the bromine count in the formula. The total M+4 intensity relative to M intensity is given by Equation 21:

$$[M+4][M]^{-1}=\tfrac{1}{2}A_{Cl}^2(C_{Cl}^2-C_{Cl})+A_{Cl}C_{Cl}A_{Br}C_{Br}+\tfrac{1}{2}A_{Br}^2(C_{Br}^2-C_{Br}) \quad (21)$$

If either $C_{Cl}$ or $C_{Br}$ is zero, Equation 21 can be divided by Equation 20 and the result rearranged to yield Equation 13. From [M], [M+2], and [M+4], the system of Equations 20 and 21 should yield a real and plausible solution for $C_{Cl}$ and $C_{Br}$.

Figure 6:
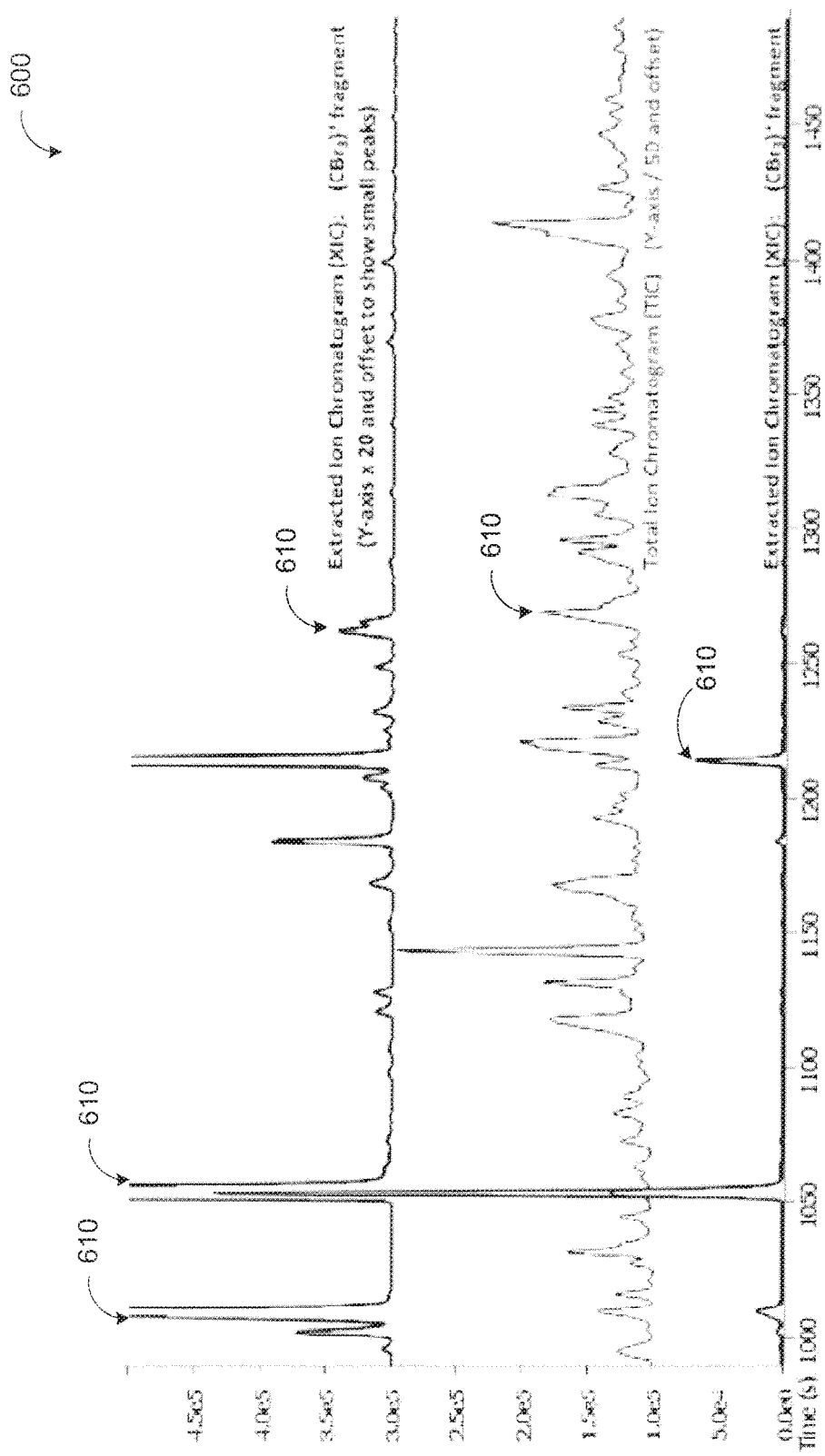
FIG. 6 shows an example extracted ion chromatogram and total ion chromatogram based on the data from the TOF-MS.

FIG. 6 shows an example extracted ion chromatogram and total ion extracted ion chromatogram 600 based on the data 140 from the TOF-MS 100. The extracted ion chromatogram total ion and extracted ion chromatogram 600 includes an x-axis for time and a y-axis for signal intensity. Individual peaks 610 are shown in the extracted ion chromatogram and total ion extracted ion chromatogram 600 related to the individual detection of ions 10 by the detector 130. The data 140 may be used to determine the mass defect of these ions. Further, the extracted ion chromatogram 600 may allow a user to select a region of interest and limit mass filtering and mass defect analysis to obtain more accurate results.

Figure 7:
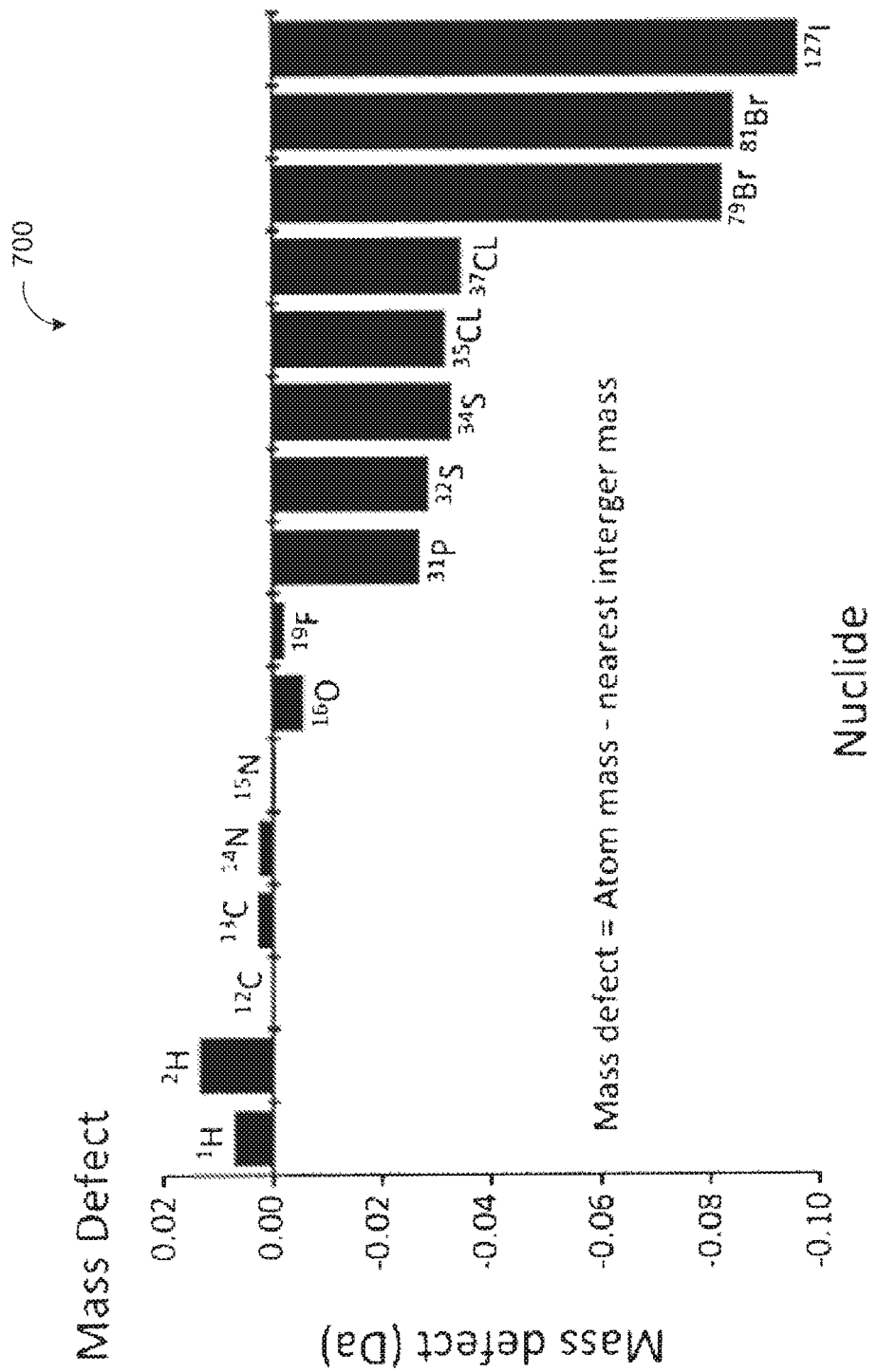
FIG. 7 shows an example graph of mass defect for some elements.

FIG. 7 shows an example graph for mass defect. The mass defect may be determined by equation 22.

$$\text{Mass Defect}=\text{Exact Mass}-\text{Nominal Mass.} \quad (22)$$

For example, the mass defect is centered around carbon having an atomic weight of 12.0000 in accordance with IUPAC. Considering $C_3H_8$, $C_3H_8$ has an exact mass of 44.06205 and a nominal mass of 44.00000, the resulting mass defect is 0.06205. By comparison, $C_3Cl_6$ has an exact mass of 281.81257 and a nominal mass of 282.00000, resulting in a mass defect of −0.18743. The graph here shows atomic mass defects for some common isotopes. For example, $^1H$ has a mass defect of less than 0.01 and $^2H$ has a mass defect of approximately 0.015, allowing them to be easily distinguished. Even isotopes with similar atomic mass may be differentiated using mass defect and have substantially different mass defect values. For example, $^{15}N$ and $^{16}O$, which have an atomic mass of 15.0001 and 15.99491 respectively have a significant difference in mass defect of approximately 0.0001 and 0.005 respectively.

Figure 8:
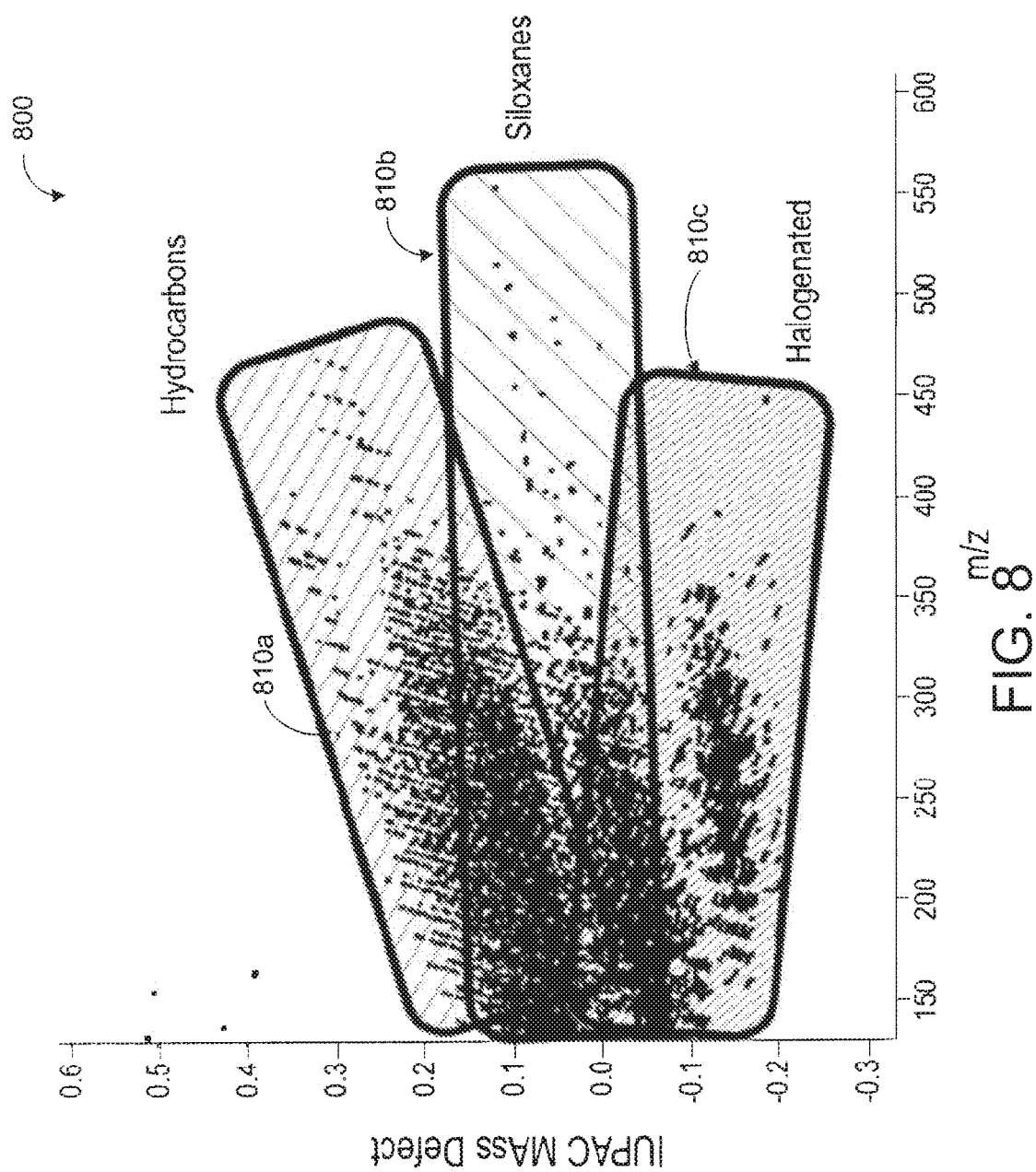
FIG. 8 shows an example mass defect plot with regions of interest

FIG. 8 shows an example mass defect plot 800 with regions 810 of interest. When the mass defect is calculated from the data 140 and plotted based on the y-axis being mass defect with Carbon 12 as zero mass defect and the m/z on the x-axis, multiple regions of interest appear. Alkanes will generally appear in the alkanes region 810a, siloxanes will generally appear in the siloxanes region 810b, and halogenated compounds will generally appear in the halogenated compound region 810c. This is useful allowing the user to identify a specific compound of interest limited to the amount of data 140 that must be processed to determine the specific ions 10 and/or compound formula.

Figure 9:
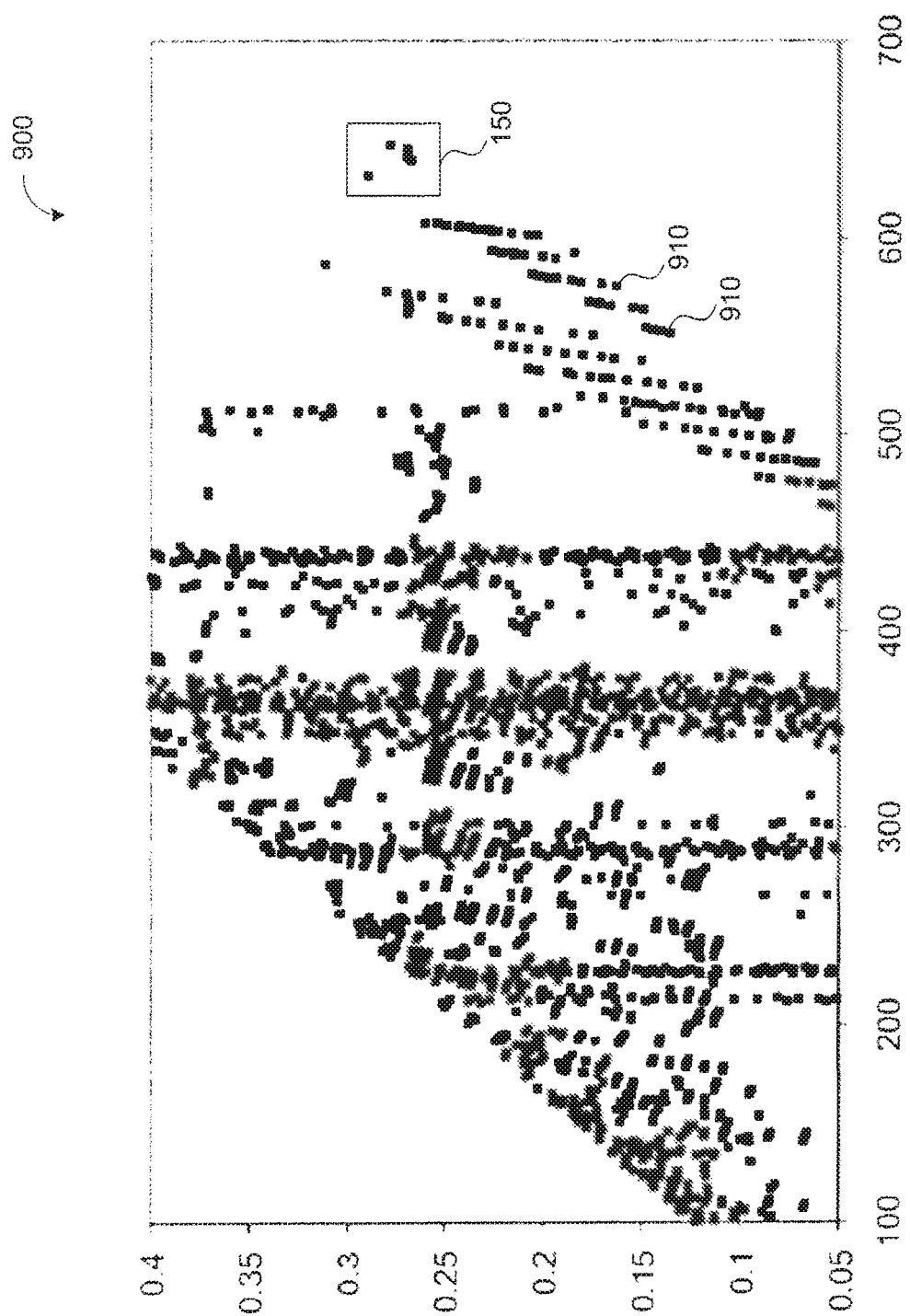
FIG. 9 shows an example Cl—H mass defect plot with Mass Defect (IUPAC) on the y-axis and m/z on the x-axis.

FIG. 9 shows an example Cl—H mass defect plot 900 with Mass Defect (IUPAC) on the y-axis and m/z on the x-axis. Alternative computations may be applied to generate a Kendrick mass defect plot where $CH_2$ is considered to be exactly 14 Da instead of the IUPAC mass for $CH_2$ which is considered to be 14.01565. The Kendrick mass is defined in equation 23.

$$\text{Kendrick Mass}=\text{IUPAC Mass}*(14.00000/14.01565) \quad (23)$$

The scaled mass defect may be determined by first solving the scaled mass of equation 24.

$$\text{Scaled mass}=\text{IUPAC mass}*\text{Scaling Factor} \quad (24)$$

The particular scaling factor for the graphs presented of Cl—H is 34/33.96048. The scaled mass defect may be determined by equation 25.

$$\text{Scaled Mass Defect}=\text{Scaled Mass}-\text{Nominal Scaled Mass} \quad (25)$$

Each point 910 on the Cl—H corresponds to a peak on the extracted ion chromatogram as seen in FIG. 6. The individual points 910 represent compounds and/or ions 10 to be identified by the computer system using operations 300 and method 400 in accordance with FIGS. 3 and 4.

Figure 10:
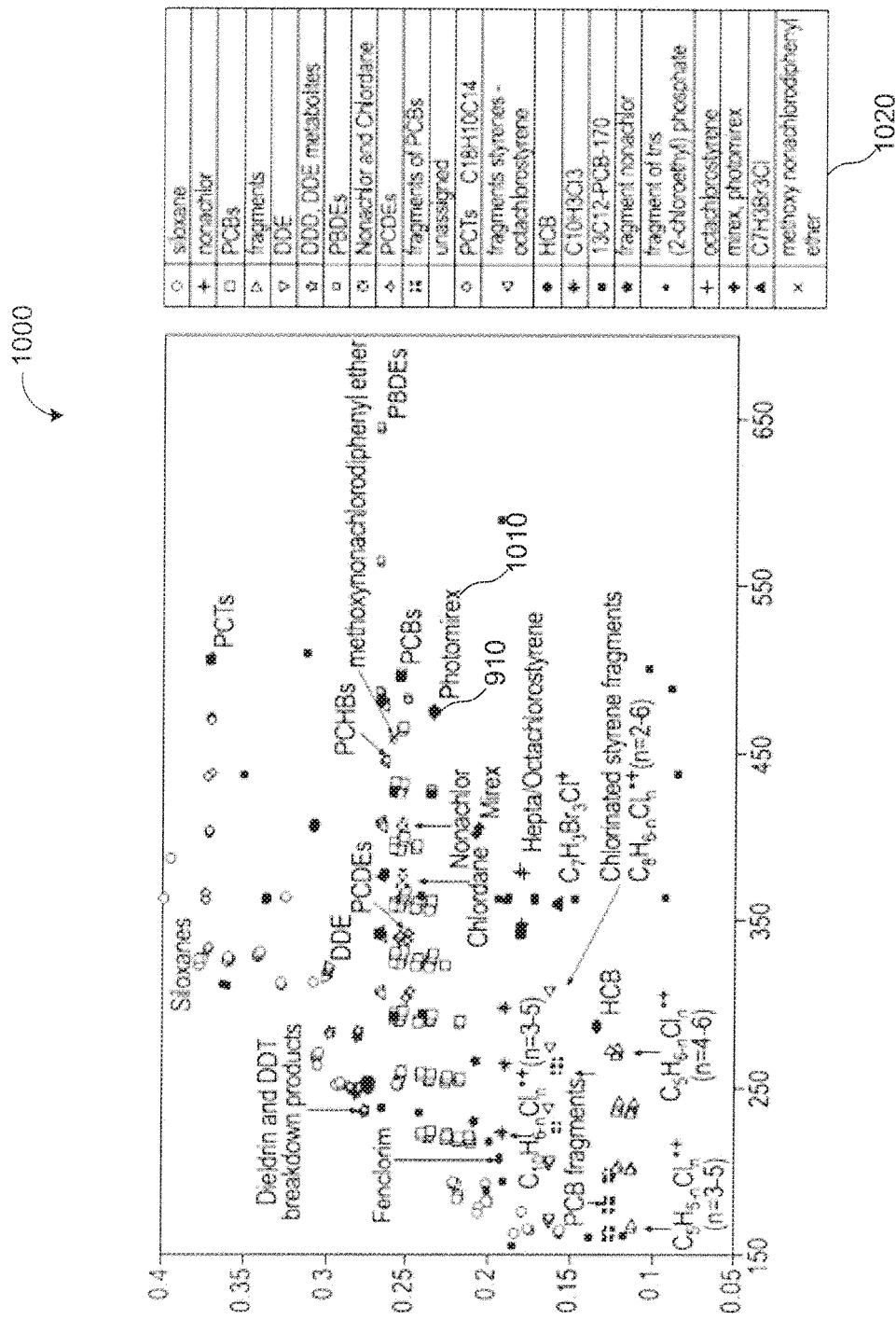
FIG. 10 shows the resulting labeled mass defect plot labeled according to the operations and method.

FIG. 10 shows the resulting labeled mass defect plot 1100 that may be labeled according to the operations 300 and method 400 in FIGS. 3 and 4. After the formula search has been performed in block 308 and the ion 10 elements identified, the mass defect plot is labeled showing individual compounds. Each dot 910 may be given a symbol or a color to identify the compound it corresponds to. Each dot 910 or compound may also include a label 1010 to make identification easier. The label 1010 may correspond to multiple dots 910. A key or index 1020 may be displayed by the computer 1100 or display to properly determine the related compound.

In at least one example, a user uses a TOF-MS 100 or other suitable mass spectrometry system to analyze a sample. The ions 10 from the sample may impact the detector 130 resulting in data 140 being delivered to a computing device 100 attached to the TOF-MS 100. The time and energy of the ions 10 impacting the detector 130 may be graphed as an ion chromatogram 600 based on the data 140 with the x-axis being the time and the y-axis being the signal intensity. The ion chromatogram 600 may be presented to the user via a display 1180 allowing the user to obtain a user selection related to a selection of data that the user is interested in. The user selection may be a click, touch gesture, caliper selection or any suitable form to select the raw or processed data the user may be interested in. A user may select a mass defect plot generation and input additional attributes including the data source, the mode, filters, reference formula, defect polarity, defect adjustment, and/or auto updating. In at least one example, the data source is caliper, the mode is scaled mass defect, the abundance filter is a minimum and has a value of 0.1, the reference formula is $CH_2$, the defect polarity is positive, the defect adjustment is 0, and auto update is enabled. The computer system 1100 may generate a mass defect plot 800, 900 based on the data source. The mass defect may be determined using equation 22 above. In at least one embodiment, the mass defect plot 800, 900 may be filtered using a specified Da value and relative abundance. In at least one embodiment, statically sound spacing and relative abundance tolerances are determined. For example, a $K_m$ value of approximately 2.8 may be used, and using equation 7 a $T_m$ (confidence interval, or m/z tolerance) may be determined based on the m/z centroid of spectral signal 1 and/or 2, expected resolving power at half-maximum height of the signals, spectra area of signal 2, ions per area for the tune mass by detector tune or measurement, and/or the m/z of the tune mass used by detector tune or detector measurement. The $T_m$ may be expanded or reduced to avoid statistically based tolerances that are too narrow at very large n or small m/z value and to avoid tolerances that are too wide at very low n and large m/z values. In some examples, the $T_m$ value is limited by a user input. Next the relative abundances of M+1 may be determined generally using equation 10, and the confidence interval may be determined using equation 12. The primary contributors to the M+1 counts are $^{13}C$, $^{15}N$, $^{29}Si$, and $^{33}S$, with minor contributions from $^{17}O$ and $^{2}H$. In some examples, the silicon equation 10 may be used. Equations 10 and 11 may be determined based on the intensity of the putative M+1 signal, the intensity of the monoisotopic signal, and the terrestrial natural abundance of the element in question. Equation 12 also includes the predicted count of an element, the element count confidence interval divided by σ, and the total number of ions in the pair of putative isotopologue signals. Next the M+2 signals may be determined. In some examples, the relative abundance tolerances are determined separately in chlorinated or brominated isotope patterns using equations 13-16 based on the predicted maximum count of an "M+2" element (principally Cl, Br), the intensity of putative monoisotopic signal, the intensity of putative M+2 signal, the intensity of putative M+4 signal, the intensity of putative M+6 signal, the intensity of putative M+8 signal, and A is the terrestrial natural isotopic abundance (principally $^{37}Cl$, $^{81}Br$). In other examples where there is a high amount of brominated analytes, equations 17-19 may be used to determine the minimum monoisotopic mass of the brominated analyte based on the Br count predicted by the number of Br isotopologues and the Minimum Ccount required to support the Br count. In examples where there is mixed halogen patterns, such as Cl and Br, equations 20 and 21 may be used to determine the M+2 and M+4 intensity based on the terrestrial natural abundance of $^{37}Cl$, the chlorine count in the formula, the terrestrial natural abundance of $^{81}Br$, and the bromine count in the formula. The resulting values may be used to filter the data 140 into isotope patterns 150 and isotopic clusters 152. The computing device 1100 may select the most abundant unidentified ion 10 in the selected data and determine the isotopic pattern 150 for the isotopic cluster 152. Formula searching may be performed to determine elements identified by the isotopic pattern 150. For example, with an isotopic pattern for chlorine, formulas containing chlorine would be searched. In some examples, common elements, such as Carbon, Hydrogen, Nitrogen, Oxygen, Sulfur, and/or Phosphorus are also searched to determine if the formula contains these elements to determine if the unidentified ion matches the formula mass defect. After determining the formula for the unidentified ion, the computer system 1100 may label the unidentified ion 10 on a labeled mass defect plot 1000, and the computer system may color and/or mark the displayed ion 10 on the labeled mass defect plot 1000. After identifying the ion 10, the computer system 1000 searches homologous series (±Cl or ±Br), and RDBE related species (±H or ±2H) and labeling with the same color or identifier as the isotope cluster 152. In some examples, the user may select an ion 10 or the computer system may select an ion 10 and display to the user an extracted ion chromatogram±mass tolerance with the peaks 610 for the ion identified.

Figure 11:
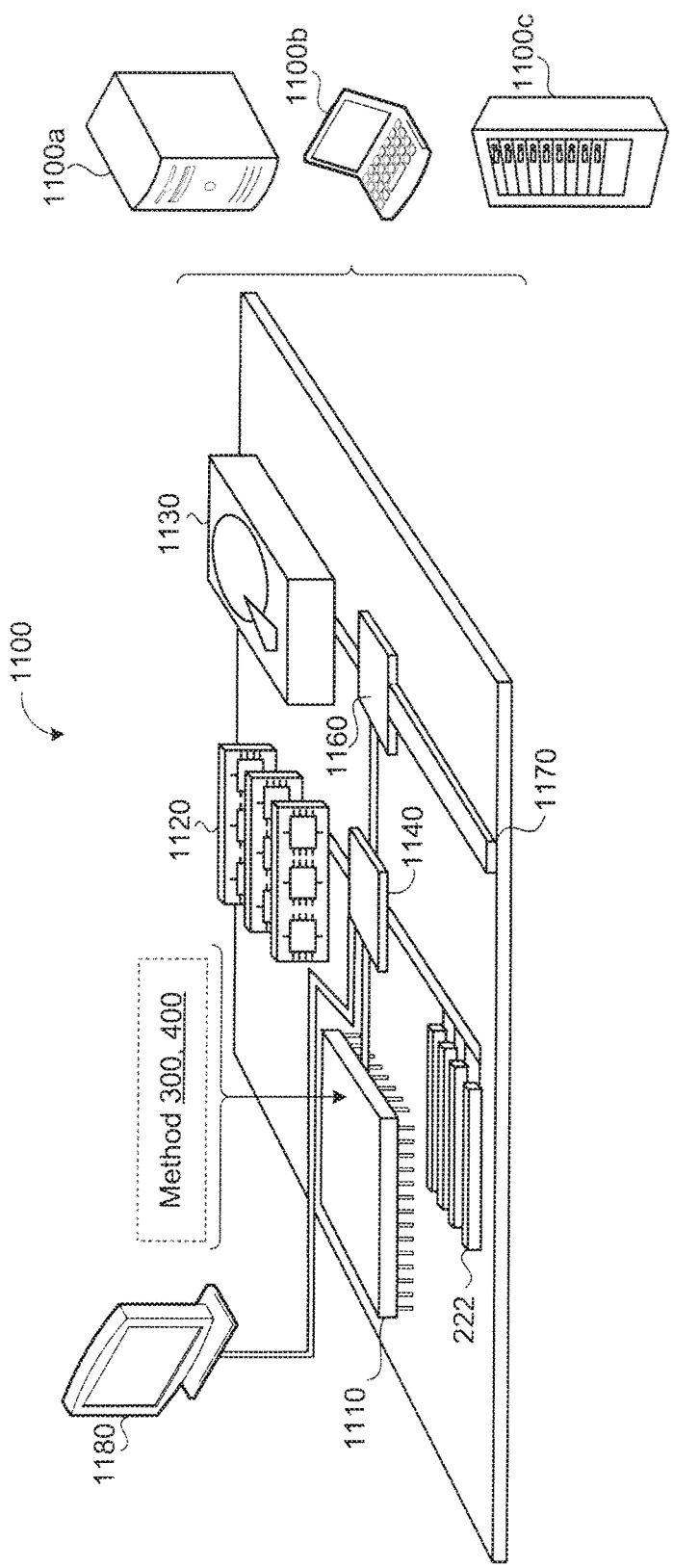
FIG. 11 is schematic view of an example computing device that may be used to implement the systems and methods described in this document.

FIG. 11 is schematic view of an example computing device 1100 that may be used to implement the systems and methods described in this document. The computing device 1100 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 1100 includes a processor 1110, memory 1120, a storage device 1130, a high-speed interface/controller 1140 connecting to the memory 1120 and high-speed expansion ports 1150, and a low speed interface/controller 1160 connecting to low speed bus 1170 and storage device 1130. Each of the components 1110, 1120, 1130, 1140, 1150, and 1160, are interconnected using various busses, and may be mounted on a common motherboard or in other manners as appropriate. The processor 1110 can process instructions for execution within the computing device 1100, including instructions stored in the memory 1120 or on the storage device 1130 to display graphical information for a graphical user interface (GUI) on an external input/output device, such as display 1180 coupled to high speed interface 1140. In other implementations, multiple processors and/or multiple buses may be used, as appropriate, along with multiple memories and types of memory. Also, multiple computing devices 1100 may be connected, with each device providing portions of the necessary operations (e.g., as a server bank, a group of blade servers, or a multi-processor system).

The memory 1120 stores information non-transitorily within the computing device 1100. The memory 1120 may be a computer-readable medium, a volatile memory unit(s), or non-volatile memory unit(s). The non-transitory memory 1120 may be physical devices used to store programs (e.g., sequences of instructions) or data (e.g., program state information) on a temporary or permanent basis for use by the computing device 1100. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 1130 is capable of providing mass storage for the computing device 1100. In some implementations, the storage device 1130 is a computer-readable medium. In various different implementations, the storage device 1130 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 1120, the storage device 1130, or memory on processor 1110.

The high speed controller 1140 manages bandwidth-intensive operations for the computing device 1100, while the low speed controller 1160 manages lower bandwidth-intensive operations. Such allocation of duties is exemplary only. In some implementations, the high-speed controller 1140 is coupled to the memory 1120, the display 1180 (e.g., through a graphics processor or accelerator), and to the high-speed expansion ports 1150, which may accept various expansion cards (not shown). In some implementations, the low-speed controller 1160 is coupled to the storage device 1130 and low-speed expansion port 1170. The low-speed expansion port 1170, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 1100 may be implemented in a number of different forms, as shown in the figure. For example, it may be implemented as a standard server 1100a or multiple times in a group of such servers 1100a, as a laptop computer 1100b, or as part of a rack server system 1100c.

Various implementations of the systems and techniques described here can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally, remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A method of constructing a filtered mass defect plot based on mass data acquired from a mass spectrometer, the method comprising:
   generating a mass defect plot from data obtained from the mass spectrometer;
   selecting an unidentified ion,
   determining an isotope pattern for the unidentified ion;
   identifying one or more elements indicated by an isotope pattern for the unidentified ion;
   searching formulas containing one or more elements indicated by the isotope pattern for the unidentified ion;
   determining a chemical formula of the unidentified ion;
   displaying the chemical formula for the unidentified ion on a screen;
   receiving a user selection of an ion;
   displaying the selected ion as an extracted ion chromatogram ±mass tolerance; and
   identifying one or more chromatographic peak corresponding to the extracted ion chromatogram ±mass tolerance.

2. The method of claim 1 further comprising identifying homologous series and deuterium and/or hydrogen related to the unidentified ion.

3. The method of claim 2, wherein the formulas in the homologous series contain elements with characteristic isotopologues that include chlorine and bromine.

4. The method of claim 1, the data is raw data from the mass spectrometer.

5. The method of claim 1, the data is deconvoluted data from the mass spectrometer.

6. The method of claim 1, further comprising labeling the chemical formulas for the unidentified ion on the screen.

7. The method of claim 1, further comprising assigning a color or identifier to the unidentified ion on the screen.

8. The method of claim 1, the mass defect plot is an iterative addition of a chemical formula.

9. The method of claim 8, wherein the mass defect plot is a $CH_2$ mass defect plot.

10. The method of claim 1, further comprising filtering all ions in the mass defect plot that do not have an associated isotopologue ion by filtering the mass defect with a specific relative abundance tolerance.

11. The method of claim 1, further comprising filtering all ions in the mass defect plot that do not have an associated isotopologue ion by comprises filtering all ions that do not match $Br_x$ isotope pattern, wherein x is an integer between 1 up to and including 15.

12. The method of claim 1, further comprising filtering all ions in the mass defect plot that do not have an associated isotopologue ion by filtering all ions that do not match $Cl_y$ isotope pattern, wherein y is an integer between 1 up to and including 15.

13. The method of claim 1, further comprising filtering all ions in the mass defect plot that do not have an associated isotopologue ion by filtering all ions that do not match $Br_xCl_y$ isotope pattern, wherein x is an integer between 1 up to and including 15 and y is an integer between 1 up to and including 15.

14. The method of claim 1, further comprising filtering all ions in the mass defect plot that do not have an associated isotopologue ion by filtering by determining a spacing tolerance.

15. The method of claim 14, wherein the spacing tolerance is based on a static m/z distance between a first signal and a second signal.

16. The method of claim 15, wherein a m/z space tolerance is based on a statistical confidence interval.

17. The method of claim 15, wherein the spacing tolerance is further based on a number of ions in the first signal, and a number of ions in the second signal.

18. The method of claim 14, wherein the spacing tolerance is limited by an user input.

19. The method of claim 14, wherein filtering all ions in the mass defect plot that do not have an associated isotopologue ion filtering by determining a relative abundance.

20. The method of claim 19, wherein the relative abundance is determined for a M+1 signals.

21. The method of claim 20, wherein determining the relative abundance for a M+1 signals further comprises determining a maximum predicted count of an M+1 element based on an intensity of a putative M+1 signal, an intensity of a putative monoisotopic signal, and a terrestrial natural abundance of the M+1 element.

22. The method of claim 21, wherein the M+1 element is carbon, nitrogen, or silicon.

23. The method of claim 19, wherein the relative abundance is determined for a M+2 signals.

24. The method of claim 23, wherein determining the relative abundance for M+2 signals further comprises determining a maximum predicted count of an M+2 element based on an intensity of a putative monoisotopic signal, an intensity of a putative M+2 signal and a terrestrial natural abundance of the M+2 element.

25. The method of claim 23, wherein determining the relative abundance for M+2 signals further comprises determining a maximum predicted count of an M+2 element based on an intensity of a putative monoisotopic signal, an intensity of a putative M+2 signal, an intensity of a putative M+4 signal and a terrestrial natural abundance of the M+2 element.

26. The method of claim 23, wherein determining the relative abundance for M+2 signals further comprises determining a maximum predicted count of an M+2 element based on an intensity of a putative monoisotopic signal, an intensity of a putative M+4 signal, an intensity of a putative M+6 signal and a terrestrial natural abundance of the M+2 element.

27. The method of claim 23, wherein determining the relative abundance for M+2 signals further comprises determining a maximum predicted count of an M+2 element based on an intensity of a putative monoisotopic signal, an intensity of a putative M+6 signal, an intensity of a putative M+8 signal and a terrestrial natural abundance of the M+2 element.

28. The method of claim 23, wherein determining the relative abundance for M+2 signals further comprises:
determining if one or more analytes contain both chlorine and bromine; and
if the one or more analytes contain both chlorine and bromine determining a maximum predicted count of an M+2 element based on a terrestrial natural abundance of $^{37}$Chlorine, a terrestrial natural abundance of $^{81}$Bromine.

29. The method of claim 1, the filtered mass defect plot is a halogen filtered mass defect plot.

30. The method of claim 1, further comprising:
filtering all ions in the mass defect plot that do not have an associated confirmatory isotopologue.

31. A device comprising:
a display;
data processing hardware in communication with the display; and
memory hardware in communication with the data processing hardware, the memory hardware storing instructions that when executed on the data processing hardware cause the data processing hardware to perform operations comprising:
generating a mass defect plot from data obtained from a mass spectrometer;
filtering all ions in the mass defect plot that do not have an associated isotopologue;
selecting an unidentified ion;
determining an isotope pattern for the unidentified ion;
identifying one or more elements indicated by the isotope pattern for the unidentified ion;
searching formulas containing one or more elements indicated by the isotope pattern for the unidentified ion;
determining a chemical formula related to the unidentified ion;
displaying the chemical formulas for the unidentified ion on a display;
receiving a user selection of an ion;
displaying the selected ion as an extracted ion chromatogram ±mass tolerance; and
identifying one or more chromatographic peak(s) corresponding to the extracted ion chromatogram ±mass tolerance.

32. The device of claim 31, wherein the operations further comprise, identifying homologous series and deuterium and/or hydrogen related to the unidentified ion.

33. The device of claim 32, wherein the formulas in the homologous series contain elements with characteristic isotopologues that comprise chlorine and or bromine.

34. The device of claim 31, wherein the data is raw data from a mass spectrometer.

35. The device of claim 31, wherein the data is deconvoluted data from a mass spectrometer.

36. The device of claim 31, wherein the operations further comprise, labeling the chemical formulas for the unidentified ion on the display.

37. The device of claim 31, wherein the operations further comprise assigning a color to the unidentified ion on the display.

38. The device of claim 31, wherein the mass defect plot is an iterative addition of a chemical formula such as a $CH_2$ mass defect plot or the like.

39. The device of claim 31, wherein the operation filtering all ions in the mass defect plot that do not have an associated isotopologue ion, filtering the mass defect with a specific relative abundance tolerance.

40. The device of claim 31, wherein the operation filtering all ions in the mass defect plot that do not have an associated isotopologue ion, filtering all ions that do not match $Br_x$ isotope pattern, wherein x is an integer between 1 up to and including 15.

41. The device of claim 31, wherein the operation filtering all ions in the mass defect plot that do not have an associated isotopologue ion, filtering all ions that do not match $Cl_y$ isotope pattern, wherein y is an integer between 1 up to and including 15.

42. The device of claim 31, wherein the operation filtering all ions in the mass defect plot that do not have an associated isotopologue ion, filtering all ions that do not match $Br_xCl_y$ isotope pattern, wherein x is an integer between 1 up to and including 15 and wherein y is an integer between 1 up to and including 15.

43. The device of claim 31, wherein the operation filtering all ions in the mass defect plot that do not have an associated isotopologue ion, filtering by determining a spacing tolerance.

44. The device of claim 43, wherein the spacing tolerance is based on a statistical m/z confidence interval, a first signal, and a second signal.

45. The device of claim 44, wherein the m/z spacing tolerance is based on a statistical confidence interval.

46. The device of claim 44, wherein the spacing tolerance is further based on a number of ions in the first signal, and a number of ions in the second signal.

47. The device of claim 43, wherein the spacing tolerance is limited by an user input.

48. The device of claim 43, wherein the operation filtering all ions in the mass defect plot that do not have an associated isotopologue ion, filtering by determining a relative abundance.

49. The device of claim 48, wherein the relative abundance is determined for a M+1 signals.

50. The device of claim 49, wherein the operation determining the relative abundance for a M+1 signals further comprises, determining a maximum predicted count of an M+1 element based on an intensity of a putative M+1 signal, an intensity of a putative monoisotopic signal, and a terrestrial natural abundance of the M+s1 element.

51. The device of claim 50, wherein the M+1 element is carbon, nitrogen, or silicon.

52. The device of claim 48, wherein the relative abundance is determined for a M+2 signals.

53. The device of claim 52, wherein the operation determining the relative abundance for M+2 signals further comprises, determining a maximum predicted count of an M+2 element based on an intensity of a putative monoisotopic signal, an intensity of a putative M+2 signal and a terrestrial natural abundance of the M+2 element.

54. The device of claim 52, wherein the operation determining the relative abundance for M+2 signals further comprises, determining a maximum predicted count of an M+2 element based on an intensity of a putative monoisotopic signal, an intensity of a putative M+2 signal, an intensity of a putative M+4 signal and a terrestrial natural abundance of the M+2 element.

55. The device of claim 52, wherein the operation determining the relative abundance for M+2 signals further comprises, determining a maximum predicted count of an M+2 element based on an intensity of a putative monoisotopic signal, an intensity of a putative M+4 signal, an intensity of a putative M+6 signal and a terrestrial natural abundance of the M+2 element.

56. The device of claim 52, wherein the operation determining the relative abundance for M+2 signals further comprises, determining a maximum predicted count of an M+2 element based on an intensity of a putative monoisotopic signal, an intensity of a putative M+6 signal, an intensity of a putative M+8 signal and a terrestrial natural abundance of the M+2 element.

57. The device of claim 52, wherein the operation determining the relative abundance for M+2 signals further comprises:
determining if one or more analytes contain both chlorine and bromine; and
if the analytes contain both chlorine and bromine determining a maximum predicted count of an M+2 element based on a terrestrial natural abundance of $^{37}$Chlorine, a terrestrial natural abundance of $^{81}$Bromine.

* * * * *